United States Patent [19]

Shortridge

[11] Patent Number: 4,605,734

[45] Date of Patent: Aug. 12, 1986

[54] BASIC DERIVATIVES OF AZO BENZENE

[76] Inventor: Douglas Shortridge, 36 Parkside Road, Leeds LS6 4QG, England

[21] Appl. No.: 654,319

[22] Filed: Sep. 25, 1984

[30] Foreign Application Priority Data

Sep. 27, 1983 [GB] United Kingdom ................. 8325755

[51] Int. Cl.$^4$ .................... C07C 107/06; A61K 31/655
[52] U.S. Cl. ..................................... 534/738; 534/616;
534/581; 534/582; 534/887
[58] Field of Search ......................................... 534/738

[56] References Cited

U.S. PATENT DOCUMENTS 3,153,033  10/1964  Steiger .................................. 534/738

FOREIGN PATENT DOCUMENTS 1902475  4/1970  Fed. Rep. of Germany ...... 534/738

Primary Examiner—Floyd D. Higel
Attorney, Agent, or Firm—Bert J. Lewen; Henry Sternberg

[57] ABSTRACT

A compound, useful as an anti-cancer drug or agent, having the formula:

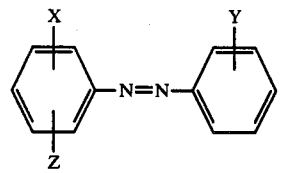

where X represents hydroxyl, amino or alkylamino, Y represents one member selected from

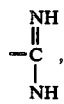

or alkylated derivatives thereof, and Z represents hydrogen or one of the basic groups of Y, an acid addition salt of the said compound, a nitrogen oxide derivative of the said compound in the case where it contains a ring nitrogen atom or atoms.

6 Claims, No Drawings

BASIC DERIVATIVES OF AZO BENZENE

This invention relates to chemical compounds useful for the purpose of cancer research and comprises a group of such compounds which exhibit activity against cancer in experimental animals.

In the field of anti-tumour compounds and compounds active against leukaemia, research is directed towards the discovery of compounds having a selective action against the tumour cell, and usually makes progress by the screening of large numbers of compounds which are chemically similar to compounds of known and established medical value. The present invention is the outcome of a theoretical approach to this subject based, inter alia, on considerations of selective bonding between the tumour cell and a compound of specific size, shape and electrical charge distribution, which can lead to the eventual destruction or control of the tumour cell.

This invention relates to materials which in the free base form are of the general structure

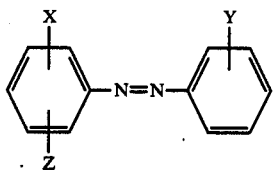

and to acid addition salts thereof where X represents hydroxy, amino or alkylamino. Y represents one of the basic groupings

where $R_1$ and $R_2$ represent hydrogen or an alkyl group. $R_1$ and $R_2$ may for instance be straight or branched chain alkyl groups. Generally lower alkyl groups are preferred, i.e., those containing less than 6 or 8 carbon atoms and preferably methyl or ethyl. The two groups $R_1$ and $R_2$ may also be united to form a further ring embracing the nitrogen atoms such as, for example, imidazoline or 1 4 5 6 tetra hydropyrimidine. Z represents either hydrogen or one of the basic groups of Y.

Either of the rings that together form the azobenzene structure may contain one or more ring nitrogen atoms.

I have discovered that materials of this general type, which may be regarded as basic derivatives of azobenzene possess anti-tumour properties.

It is a valuable feature of this invention that the materials are of low toxicity. Thus in some cases five daily doses by injection of 200 mg. compound per kilogram of body weight of control mice has been non-toxic, whilst five daily doses of as little as 12.5 mg kilogram of body weight into mice earlier injected with the P388 leukaemia has shown a significant increase in survival time.

This invention also includes compounds of the above mentioned general character in which nuclear substituents are present at one or more positions in either of the rings, e.g., halogeno, hydroxy, alkyl, alkoxy, amino, alkylamino substituents.

Compounds in accordance with the invention are active against P388 leukaemia in mice and may be administered by injection, or orally, at a dose rate of, for example, 20 to 50 mg per kilogram of animal per day.

The survival time of mice treated with these substances has been extended typically by some 50% and much longer in some cases as compared with untreated mice after implantation of the leukaemia for the control mice.

The compounds are also active against solid tumours.

The products are desirably prepared and used as the acid addition salts of any appropriate inorganic or organic acid. Materials carrying a second basic grouping as a substituent are especially preferred.

The azo compounds are made by methods well known to those skilled in the art.

It is most convenient to do so by coupling the diazonium salt derived from an aniline containing one of the basic groups of Y with an appropriate phenol or amine. It is helpful to add a small quantity of pyridine or dimethyl formamide to the reaction mixture.

It will be appreciated that the invention also embraces pharmaceutical compositions containing any of the aforementioned compounds as the active constituent and methods for preparing such compounds in a form suitable for administration.

The invention will now be further described with detailed examples of the preparation of typical compounds in the form of hydrochloride salts but these examples do not limit the invention thereto.

EXAMPLE I

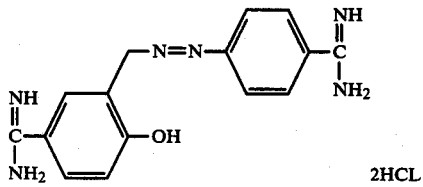

2.0 grs 4 amino benzamidine dihydrochloride are dissolved in 10 ml 2N hydrochloric acid and cooled to under 5° C. 0.7 grs sodium nitrite are dissolved in 5 ml water, cooled to under 5° C. and added to the above solution. Excess nitrous acid is removed by addition of sulphamic acid, testing with starch iodide paper. The diazonium salt solution so obtained is allowed to come to room temperature and stand for approximately 24 hours, but neither the temperature or time is critical. The solution of 4 hydroxy benzamidine so obtained is cooled to under 5° C. and the pH value adjusted to approximately 8.5 with dilute caustic soda solution.

2.0 grs 4 amino benzamidine dihydrochloride are diazotised as above. After removal of excess nitrous acid with sulphamic acid the solution is coupled with the cooled 4 hydroxy benzamidine solution, keeping the pH value at approximately 8–8.5

After coupling is complete the solution is neutralised with dilute hydrochloric acid to a pH value of about 6.5. The desired product separates out, which may be helped by cooling and adding brine, is filtered off and dried.

EXAMPLE II

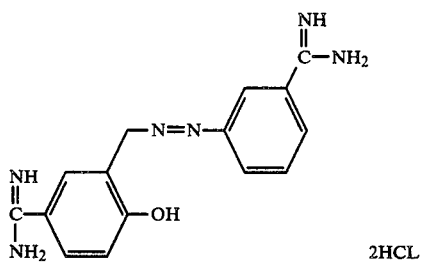

2.0 grs 4 amino benzamidine dihydrochloride are dissolved in 5 ml dimethyl formamide and 10 ml water with addition of 3 ml concentrated hydrochloric acid, and cooled to under 5° C. 0.7 grs sodium nitrite is dissolved in 5 ml water, cooled to under 5° C. and added to the above solution. Excess nitrous acid is removed with sulphamic acid, testing with starch iodide paper. The diazonium salt solution so obtained is allowed to stand at room temperature for approximately 24 hours but neither time nor temperature is critical.

The solution of 4 hydroxy benzamidine so obtained has the pH value raised to approximately 8.5 by addition of caustic soda solution, making sure that the phenol is brought into solution, which is then cooled to under 5° C.

2.0 grs 3-amino benzamidine dihydrochloride are diazotised as above and after removal of excess nitrous acid is coupled with the 4 hydroxy benzamidine, keeping the pH value at approximately 8.5 by careful addition of caustic soda solution. When coupling is complete the resultant mixture is acidified with hydrochloric acid to a pH value of about 6.5 and the desired product removed by filtration.

EXAMPLE III

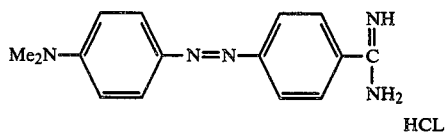

1.2 grs N N dimethylaniline are dissolved in 10 ml dimethyl formamide and 50 ml water. The pH value is brought to about 5 by addition of dilute hydrochloric acid and the solution is cooled to under 5° C.

2.0 grs 4 amino benzamidine dihydrochloride are diazotised as in Example I and coupled with the amine solution, maintaining the pH value at about 5.

The desired product is removed by filtration, washed and dried.

EXAMPLE IV

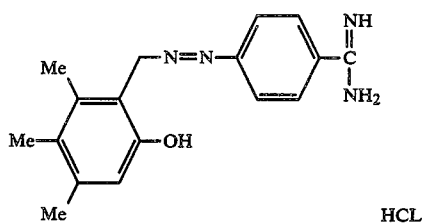

2.0 grs 3.4.5 trimethylphenol are dissolved in 10 ml pyridine and 30 ml water with addition of sufficient caustic soda to raise the pH value to approximately 8–8.5. The solution is cooled to under 5° C. and coupled with the diazonium salt prepared from 3.0 grs 4 amino benzamidine dihydrochloride as in Example I, maintaining the pH value at over about 8. When the reaction is complete the pH value is raised to about 10–11 by addition of caustic soda and the base removed by filtration, washed and dried.

The base is then dissolved in acetone and the hydrochloride precipitated by addition of hydrochloric acid.

EXAMPLE V

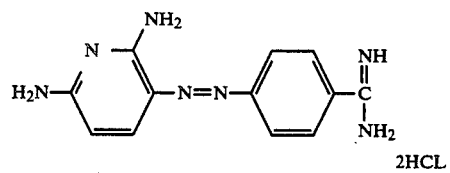

1.0 gr 2.6 diamino pyridine is coupled with the diazonium salt derived from 2.0 grs 4 amino benzamidine dihydrochloride, as in Example III.

EXAMPLE VI

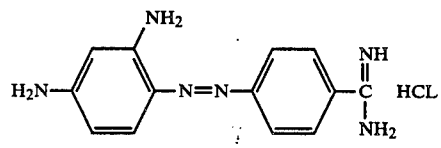

1.0 gr meta phenylene diamine is coupled with the diazonium salt derived from 2.1 grs of 4 amino benzamidine dihydrochloride as in Example III.

EXAMPLE VII

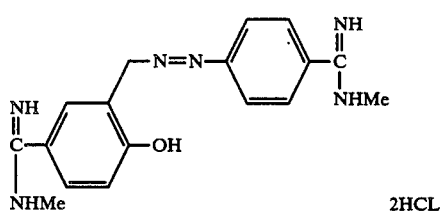

2.0 grs 4 amino N methyl benzamidine dihydrochloride are dissolved in 10 ml of 2N hydrochloric acid and cooled to under 5° C. 0.7 grs sodium nitrite are dissolved in 5 ml water, cooled to under 5° C. and added to the above solution. 3 ml pyridine are added to the solution of the diazonium salt so obtained and the pH value raised to between about 8 and 9 by careful addition of caustic soda, and then allowed to stand at ambient temperature for about 24 hours. The resultant mixture is acidified with hydrochloric acid to a pH value of about 6.5 and the desired product removed by filtration.

I claim:
1. A compound of the formula

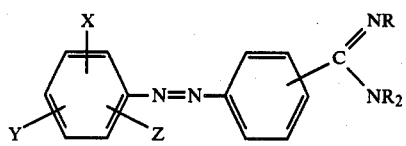

where X is —NH$_2$ or

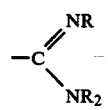

Y is hydrogen or —NH$_2$, Z is hydrogen or hydroxyl, and each R is independently hydrogen, methyl or ethyl, provided that when X is

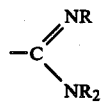

then Y is hydrogen and Z is hydroxyl and when X is —NH$_2$ then Y is —NH$_2$; or a compound of the above formula except that a ring carbon atom in either ring is replaced by a nitrogen atom; or an acid addition salt of said compounds.

2. A compound according to claim 1 wherein each R is hydrogen.

3. A compound of the formula

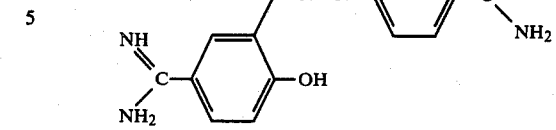

or its acid addition salts.

4. A compound of the formula

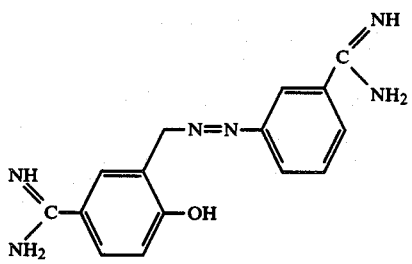

or its acid addition salts.

5. A compound of the formula

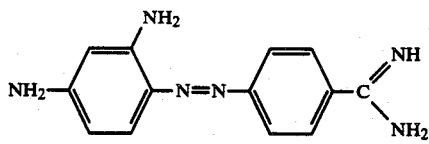

or its acid addition salts.

6. A compound of the formula

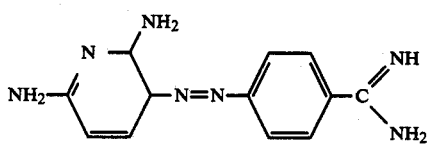

or its acid addition salts.

* * * * *